(12) United States Patent
Finch et al.

(10) Patent No.: US 6,592,564 B2
(45) Date of Patent: *Jul. 15, 2003

(54) METHODS AND KITS FOR LOCKING AND DISINFECTING IMPLANTED CATHETERS

(75) Inventors: Charles D. Finch, Clinton, MS (US); John H. Wang, North Andover, MA (US)

(73) Assignee: VascA, Inc., Tewksbury, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/359,842

(22) Filed: Jul. 23, 1999

(65) Prior Publication Data

US 2002/0082582 A1 Jun. 27, 2002

(51) Int. Cl.$^7$ ............................................. A61M 25/00
(52) U.S. Cl. .................. 604/500; 604/93.01; 604/256; 604/523
(58) Field of Search ............................ 604/500, 19, 27, 604/28, 48, 508, 513, 502, 522, 256, 93.01, 523, 264, 288.01, 265, 266, 269, 36, 181, 183

(56) References Cited

U.S. PATENT DOCUMENTS

| | | | |
|---|---|---|---|
| 4,929,242 A | | 5/1990 | Desecki et al. |
| 4,954,239 A | | 9/1990 | Mueller |
| 5,077,281 A | | 12/1991 | Reinmuller |
| 5,142,010 A | * | 8/1992 | Olstein ........................ 424/407 |
| 5,263,930 A | * | 11/1993 | Ensminger ................... 604/175 |
| 5,281,205 A | * | 1/1994 | McPherson .................. 604/267 |
| 5,358,492 A | * | 10/1994 | Feibus ......................... 604/264 |
| 5,704,915 A | * | 1/1998 | Melsky et al. ............... 604/175 |
| 5,807,356 A | | 9/1998 | Finch, Jr. et al. |
| 5,931,829 A | * | 8/1999 | Burbank et al. ............. 604/502 |
| 6,042,569 A | * | 3/2000 | Finch, Jr. et al. ............ 604/175 |
| 6,056,717 A | * | 5/2000 | Finch et al. ................... 604/93 |
| 6,059,766 A | * | 5/2000 | Greff ........................... 604/515 |
| 6,132,415 A | * | 10/2000 | Finch et al. ............ 604/288.01 |
| 6,166,007 A | * | 12/2000 | Sodemann ................... 514/152 |
| 6,299,609 B1 | * | 10/2001 | Finch et al. ................. 604/502 |
| 6,299,610 B1 | * | 10/2001 | Finch et al. ................. 604/500 |
| 6,350,251 B1 | * | 2/2002 | Prosl et al. ................ 514/222.5 |
| 6,361,524 B1 | | 3/2002 | Odell et al. |

* cited by examiner

Primary Examiner—Michael J. Hayes
Assistant Examiner—Cris L. Rodriguez
(74) Attorney, Agent, or Firm—Townsend and Townsend and Crew LLP

(57) ABSTRACT

Implanted catheters are locked with a solution comprising a lower alcohol, typically ethanol, propanol, or butanol, most preferably isopropanol. The use of an alcohol can both reduce fouling of the catheter, particularly clotting and thrombus in intravascular catheters, as well as reducing the risk of infection. The risk of infection can be further reduced by employing a catheter body which is sufficiently porous to permit the lower alcohol or other anti-microbial solution to penetrate into the catheter body and preferably through the catheter into tissue surrounding the implanted catheter.

38 Claims, 10 Drawing Sheets

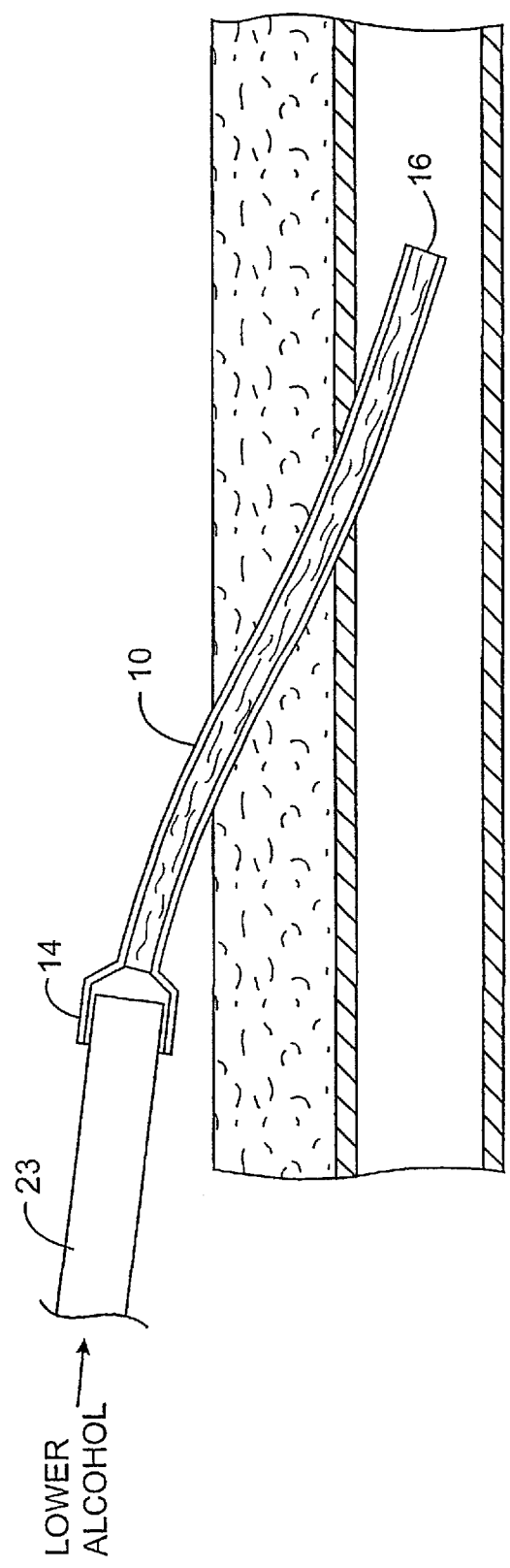

METHODS AND KITS FOR LOCKING AND DISINFECTING IMPLANTED CATHETERS

BACKGROUND OF THE INVENTION

1. Field of the Invention

The present invention relates generally to medical methods and kits. More particularly, the present invention relates to methods and kits for flushing an interior lumen of an implanted catheter prior to closing the catheter between successive uses.

Implanted catheters enjoy widespread use in a number of medical procedures. For example, intravenous (IV) therapy relies on long-term implantation of a venous catheter to deliver fluids, medications, and other substances to a patient. Hemodialysis and hemofiltration both rely on separate draw and return catheters implanted in a vein to allow extra corporeal treatment of the blood. Peritoneal dialysis, in contrast, relies on a single catheter implanted in the peritoneum to permit introduction and withdrawal of dialysate to permit in situ dialysis.

The need to leave catheters implanted over long periods of time raises a number of concerns. For example, the catheters can become infected requiring treatment of the patient and often times removal of the catheter. This is a particular problem with transcutaneous catheters where the skin penetration is a common route of infection. Secondly, implanted catheters can often become plugged or fouled over time. This is a particular problem with intravascular catheters where clotting and thrombus formation within the catheter lumen can be problematic.

To reduce problems associated with thrombus formation, it is now common to "lock" intravascular access catheters between successive uses. Locking typically involves first flushing the catheter with saline to remove blood and other substances from the catheter lumen. After the catheter has been flushed, an anti-coagulant solution, typically heparin, is then injected to displace the saline and fill the lumen. The heparin-locking solution both excludes blood from the lumen and actively inhibits clotting and thrombus formation within the lumen. While some thrombus may still form at the distal tip of the catheter, the formation is usually minimal and presents few problems. It has further been proposed to combine various anti-microbial substances with the locking solution in order to inhibit infection at the same time that thrombus is being inhibited.

While generally effective, the use of heparin locks suffers from a number of disadvantages. The need to prepare a heparin solution at the end of every catheter treatment session is time-consuming and presents an opportunity caregiver for error. Hemodialysis and hemofiltration patients will have to undergo such heparin locks at least several times a week, while patients on IV may have to undergo such heparin locks several times a day. Over time, the inconvenience and expense of performing heparin locks can build up. Moreover, the need to combine a separate anti-microbial agent in the heparin lock solution further complicates the procedure and adds expense, and the addition of an anti-microbial agent to the heparin lock will generally be effective only within the lumen and at the openings from the lumen. There will be little reduction in the risk of infection in the regions surrounding the implanted catheter, including at the point of penetration through the skin where the risk of infection is the greatest.

For all these reasons, it would be desirable to provide improved methods and kits for locking implanted catheters between successive uses. Such locking methods should inhibit fouling of the catheter lumens and/or reduce the chance of infection, preferably both. In particular, such methods and kits should be easy to implement, require minimum or no preparation, be of low cost, and be useful with most or all types of implanted catheters, including hemodialysis and hemofiltration catheters, IV catheters, peritoneal dialysis catheters, and the like. At least some of these objectives will met by the inventions described hereinafter.

2. Description of the Background Art

U.S. Pat. No. 4,929,242, describes a solution containing glycerol and having a density similar to that of blood for providing a heparin lock on an intravenous catheter. U.S. Pat. No. 5,077,281 describes an anti-microbial solution containing a taurolin compound for inhibiting coagulation in dialysis catheters and other vascular prostheses. Commonly assigned U.S. Pat. No. 5,807,356, and copending application Ser. Nos. 08/856,641; 08/896,592; 08/896,790; 08/896,791; 08/942,990; 09/003,772; 09/161,044; 09/161,068; and 09/248,156, are relevant to the present application. All of the above patents and pending applications are incorporated herein by reference.

SUMMARY OF THE INVENTION

The present invention provides methods and kits for the improved locking and/or disinfection of subcutaneously and transcutaneously implanted catheters. The catheters typically will have a distal end which is open to a body lumen. Most commonly, the catheters will be intravascular catheters where the distal end is implanted in or attached to a blood vessel, usually a vein, but in some cases an artery. Exemplary intravascular catheters include hemodialysis and hemofiltration catheters, intravenous catheters, and the like. Intravenous catheters can be used for a wide variety of purposes, including fluid infusion, drug delivery, and the like. Catheters attached other than to the vasculature include peritoneal dialysis catheters which are open to the peritoneal cavity, and the like.

The catheters which are treated by the methods of the present invention may be transcutaneously implanted or subcutaneously implanted. By "transcutaneously implanted," it is meant that the distal end of the catheter is attached to or implanted within a target body lumen and a proximal end of the catheter is located externally to the patient. An intermediate portion of the catheter will thus pass through or penetrate the patient's skin, and the proximal end of the catheter will usually have a hub to permit selective attachment of infusion tubes, syringes, solution bags, and the like. Most commonly, the proximal attachment hub will have a luer fitting. By "subcutaneously implanted," it is meant that the entire catheter is implanted beneath the skin and no portion of the catheter extends through the skin. Such subcutaneously implanted catheters are typically attached to a fully implanted hub at their proximal ends. The hub permits percutaneous access via a needle or other penetrating element. After a treatment session is finished, the needle or other penetrating element is removed and all portions of the catheter and proximal hub are then located beneath the skin. Examples of such subcutaneously implanted catheters and proximal access hubs are described in the commonly assigned, copending applications described above, as well as U.S. Pat. No. 5,807,356, the full disclosures of which have previously been incorporated herein by reference.

As described in the Background section above, both transcutaneously and subcutaneously implanted catheters are subject to fouling and plugging, particularly in and about their distal ends which are implanted in or attached to a blood vessel or other body lumen. To reduce the risk of such fouling, the present invention provides and methods and kits for filling a lumen of the implanted catheter with a lower alcohol, typically ethanol, propanol, or butanol, preferably isopropanol. Surprisingly, it has been found that these lower alcohols are effective in inhibiting fouling and plugging of the lumen, particularly in inhibiting clot formation within the lumens of intravascular catheters. The ability to inhibit clot formation without the need to prepare and use heparin solutions is a significant advantage. Moreover, the lower alcohols have the additional ability to inhibit infection without the need to incorporate any additional active agents or materials. Thus, both the reduction of catheter fouling and the inhibition of infection can be achieved with the use of a commonly available, widely accepted material which is introduced to the catheter lumen in a convenient fashion, as described in more detail below.

The ability to inhibit or prevent infection of the implanted catheter can be improved by utilizing catheters where at least a portion of the catheter body is sufficiently porous to allow the lower alcohol or other disinfecting material to permeate the catheter body and, preferably, pass outwardly into the tissue region surrounding the catheter. While the use of such porous or partially porous catheter bodies can be beneficial with many anti-microbial locking solutions, such as that taught in U.S. Pat. No. 5,077,281, the full disclosure of which has been incorporated herein by reference, it is particularly useful with the lower alcohols of the present invention. It will be appreciated that the lower alcohols have relatively low molecular weights and polar structures which will enable them to readily penetrate into and optionally through many porous materials. Exemplary porous materials for construction of the catheter body include silicone rubber, expanded PTFE (e.g., GORE-TEX®, medical membranes) and the like. Such materials may be formed into the tabular catheter bodies or may be incorporated as separate component(s) into the catheter bodies.

In a first aspect, methods according to the present invention for locking an implanted catheter comprise filling a lumen of the catheter with a lower alcohol, where the lumen is open to a body lumen, typically a blood vessel, the peritoneum, or the like. The lower alcohol is selected from the group consisting of ethanol, propanol, and butanol, with the presently preferred alcohol being isopropanol. The lower alcohol may be pure, but will more usually be in aqueous solution, typically at 1% to 100% by volume, usually from 50% to 100% by volume. The implanted catheter may be a transcutaneous catheter attached at its distal end to the blood vessel, the peritoneal cavity, or the like. Alternatively, the implanted catheter may be a subcutaneously implanted catheter which is attached at its distal end to a blood vessel, the peritoneal cavity, or the like.

In a second aspect, a method according to the present invention for disinfecting an implanted catheter comprises introducing an anti-microbial solution into a lumen catheter, wherein at least a portion of the catheter is sufficiently porous to permit diffusion of the anti-microbial solution outwardly from the lumen into the catheter body, and preferably into tissue surrounding the catheter to inhibit or prevent infection. Exemplary and preferred anti-microbial solutions include lower alcohols, preferably ethanol, propanol, or butanol, and most preferably isopropanol, as described above. The implanted catheters may be subcutaneously or transcutaneously implanted.

In a third aspect of the present invention, a kit for locking an implanted catheter comprises a container (optionally a syringe) holding a volume of a lower alcohol and instructions for use setting forth a method comprising filing a lumen of the catheter with the lower alcohol. The kit may further comprise a package for holding both the container and the instructions for use, such as a box, tray, tube, pouch, or the like. The lower alcohol is typically selected from the group consisting of ethanol, propanol, and butanol, preferably being isopropanol. The volume of lower alcohol in the container is typically in the range from 1 ml to 20 ml, preferably from 2 ml to 10 ml, usually being about 2 ml to 4 ml. Additionally, the container will usually comprise a syringe to permit direct introduction of the lower alcohol into the implanted catheter.

BRIEF DESCRIPTION OF THE DRAWINGS

FIGS. 1A and 1B illustrate methods according to the present invention for locking and disinfecting a transcutaneous catheter.

DESCRIPTION OF THE SPECIFIC EMBODIMENTS

Figure 1A:
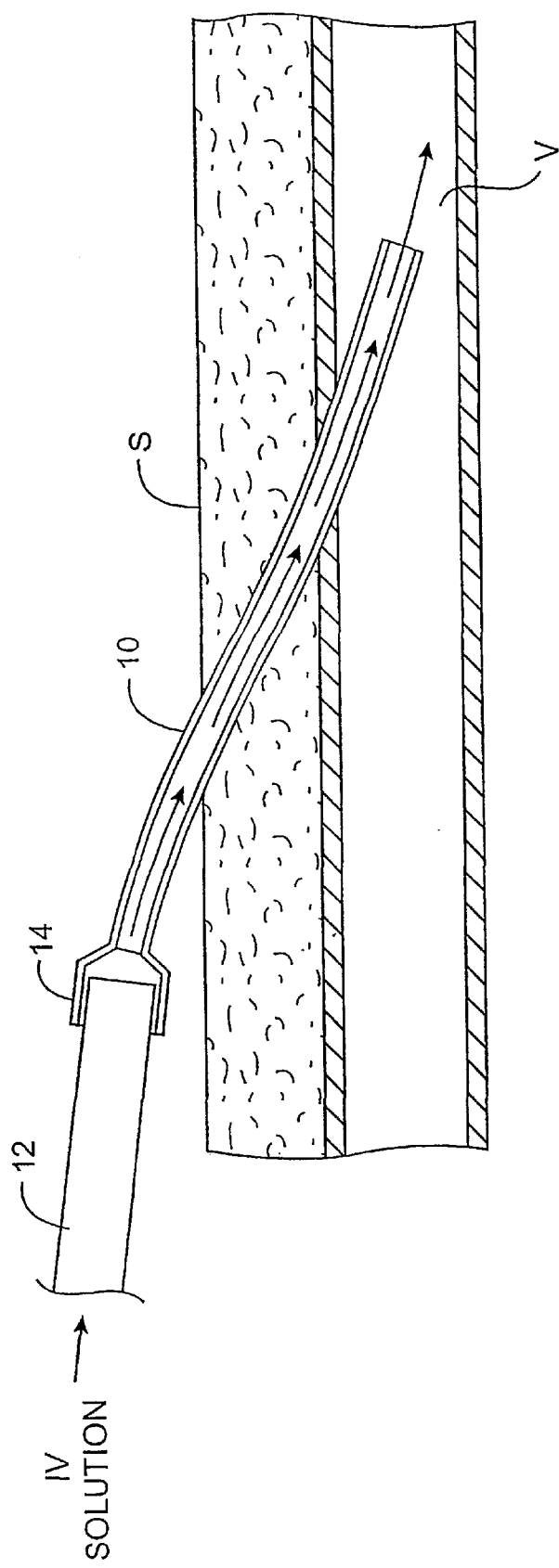

Referring now to FIGS. 1A and 1B, a method according to the present invention for locking a transcutaneously implanted venous catheter 10 will be described. The venous catheter 10 will be implanted through a patient's skin S into a vein V for infusion of the patient. When it is desired to disconnect the patient from the source of infusion, it will be necessary to lock the catheter to inhibit plugging and fouling caused by coagulation, and preferably to further inhibit the risk of infection. Shown in FIG. 1A, a tube 12 containing an IV solution will normally be connected to the proximal hub 14 of the catheter 10. The IV line 12 will be disconnected, and the catheter 10 usually flushed with saline or other flushing solution. After the flushing is completed, a lower alcohol can be introduced to fill the inner lumen of the catheter 10, as shown in FIG. 1B. Usually, a sufficient volume of the lower alcohol (as set forth above) will be introduced to completely fill the lumen, with minimum excess passing from distal end 16 of the catheter. The loss of excess alcohol into a blood vessel or most other body lumens, however, will generally not be a problem. The "column" of the lower alcohol will then occupy the inner lumen, and the proximal hub 14 will be sealed, helping retain the lower alcohol in place. It has been found that the lower alcohol will both inhibit clotting and coagulation at the distal end 16 as well as inhibit infection throughout the catheter. When it is desired to reattach the patient to the IV source, the lower alcohol will be removed and the catheter lumen flushed with saline.

Figure 2A:
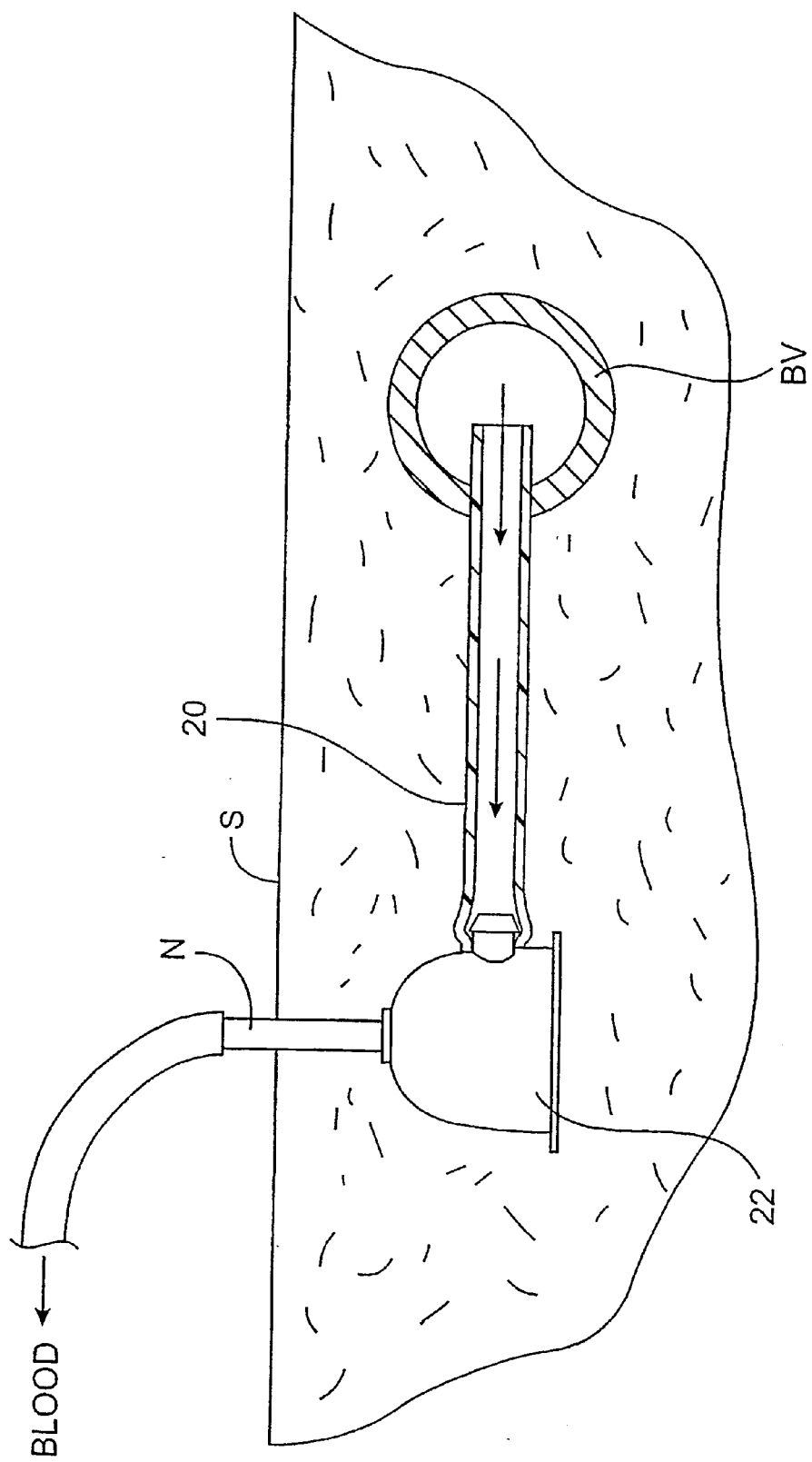
FIGS. 2A–2C illustrate methods according to the present invention for locking and disinfecting a subcutaneously implanted catheter.

Referring now FIGS. 2A–2C, locking of a subcutaneously implanted catheter 20 used for hemodialysis access will be described. The catheter 20 is implanted between a target blood vessel BV, typically a vein, and an implanted port 22.

During hemodialysis, blood may be withdrawn through the catheter 20, through the port 22 and externally through a needle N and connecting line 23 used to percutaneously access the port 22. Alternatively, the port and catheter could be used to return treated blood to the patient. As described in the copending applications incorporated by reference above, the port and catheter combinations are typically used in pairs to permit both blood withdrawal and blood return.

Figure 2B:
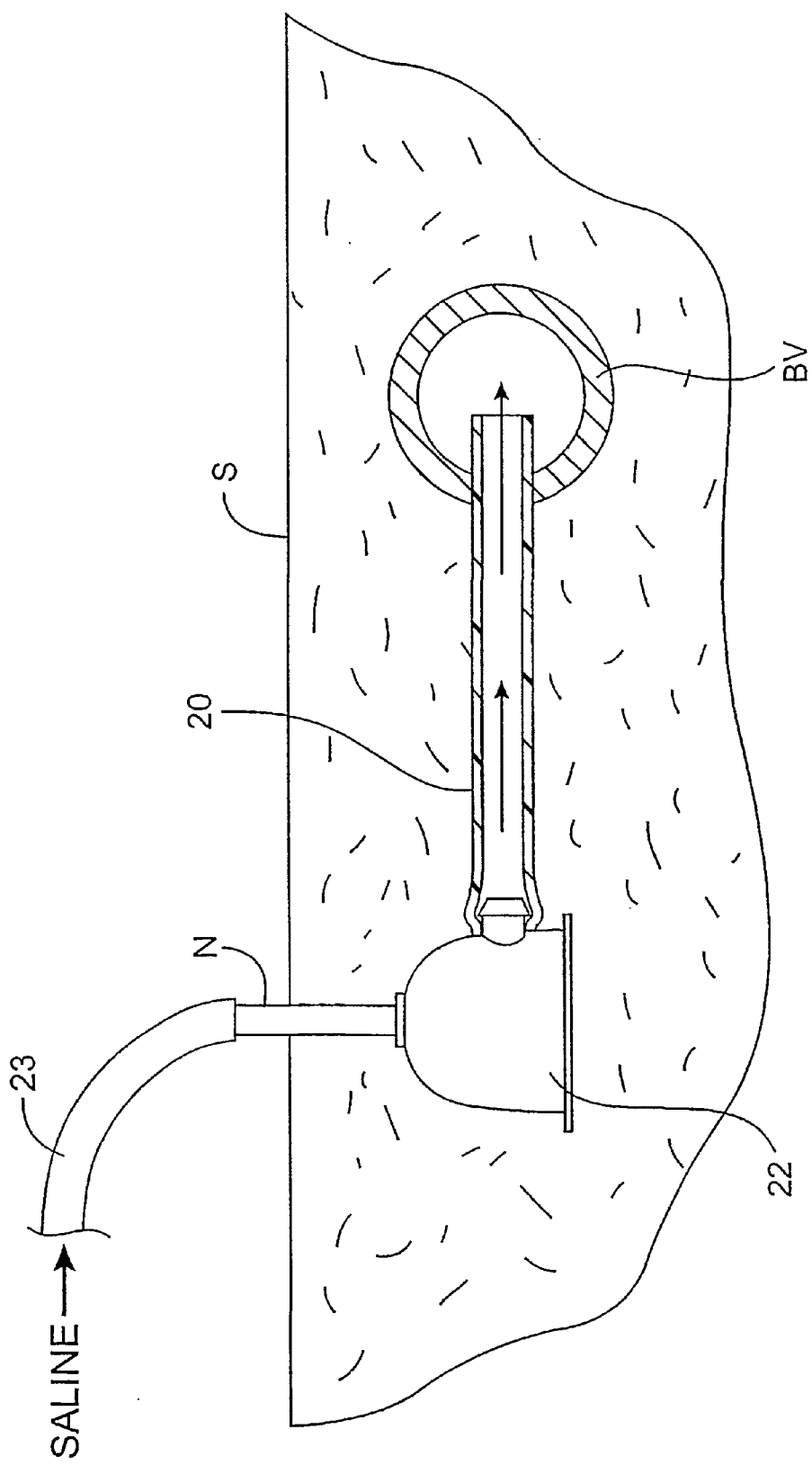
Figure 2C:
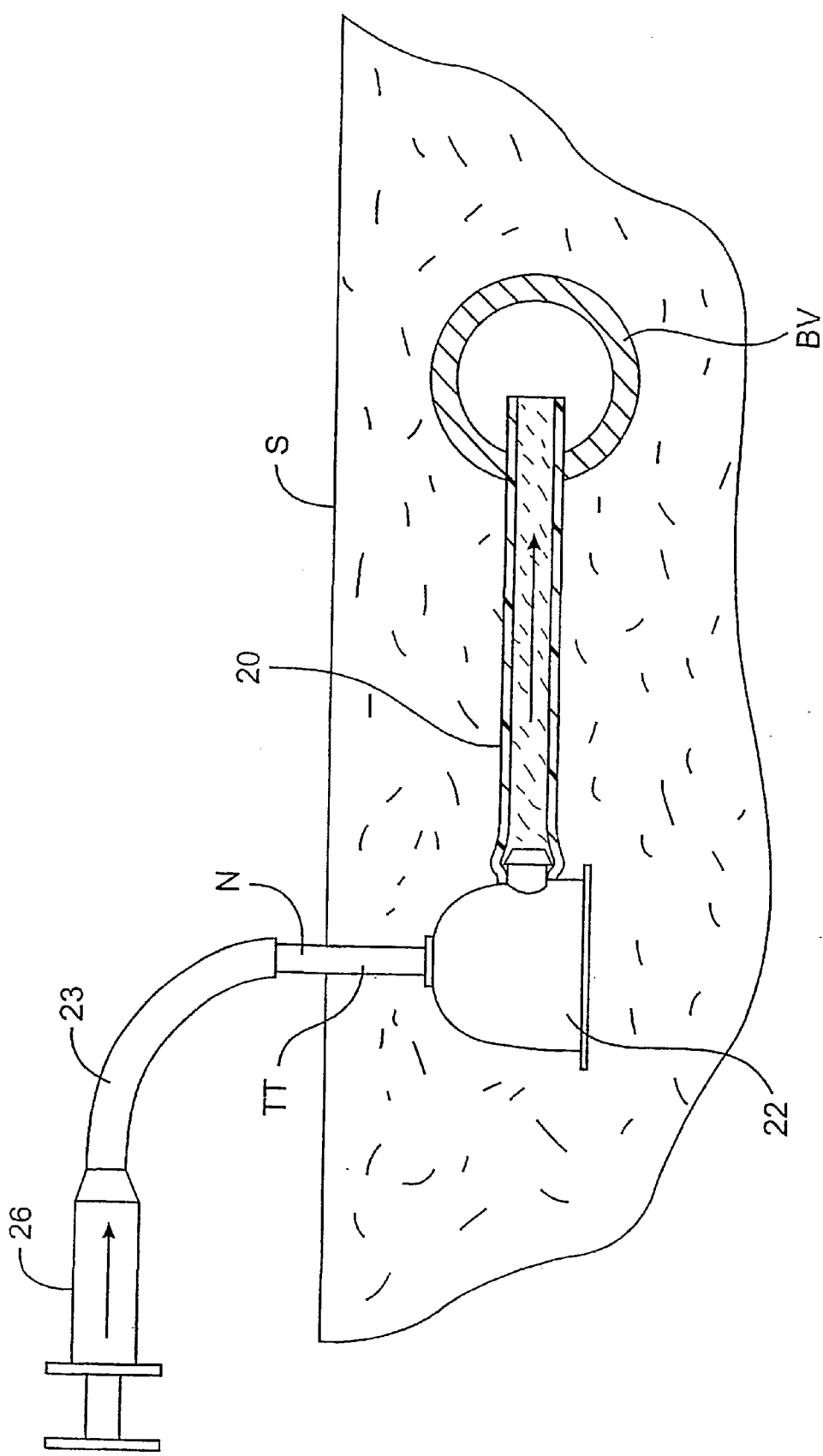

When it is desired to end a hemodialysis (or hemofiltration) treatment, saline will be introduced through the needle N (typically from a syringe which is attached to the connecting line 23) to flush the lumen, as shown in FIG. 2B. After the flush is complete, a container such as syringe 26 containing the lower alcohol is injected through the port 22/line 23 and into the lumen of catheter 20 to displace the saline and lock the catheter. The lower alcohol will remain in place within the catheter 20 after the needle end is withdrawn and the valve 22 closed to seal off the proximal end of the catheter 20. As a particular advantage, residual alcohol in the needle will be dispersed in the tissue tract TT left by the needle as well as in portions of the port 22 upstream of its internal valve. The presence of the alcohol or other anti-microbial solution will further inhibit infection in both the port and tissue tract.

Figure 3A:
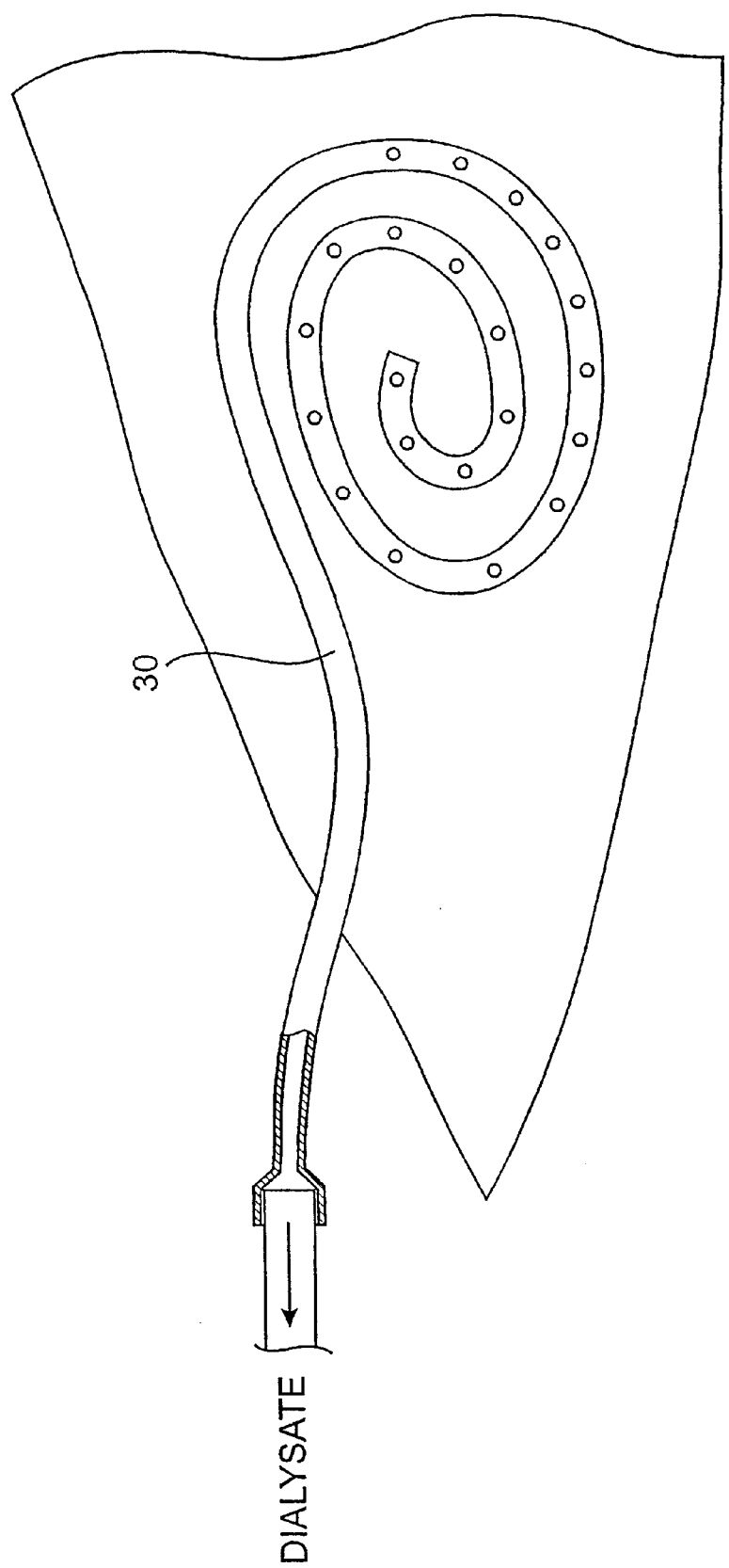
FIGS. 3A–3C illustrate methods according to the present invention for locking and disinfecting a peritoneal dialysis catheter.
Figure 3B:
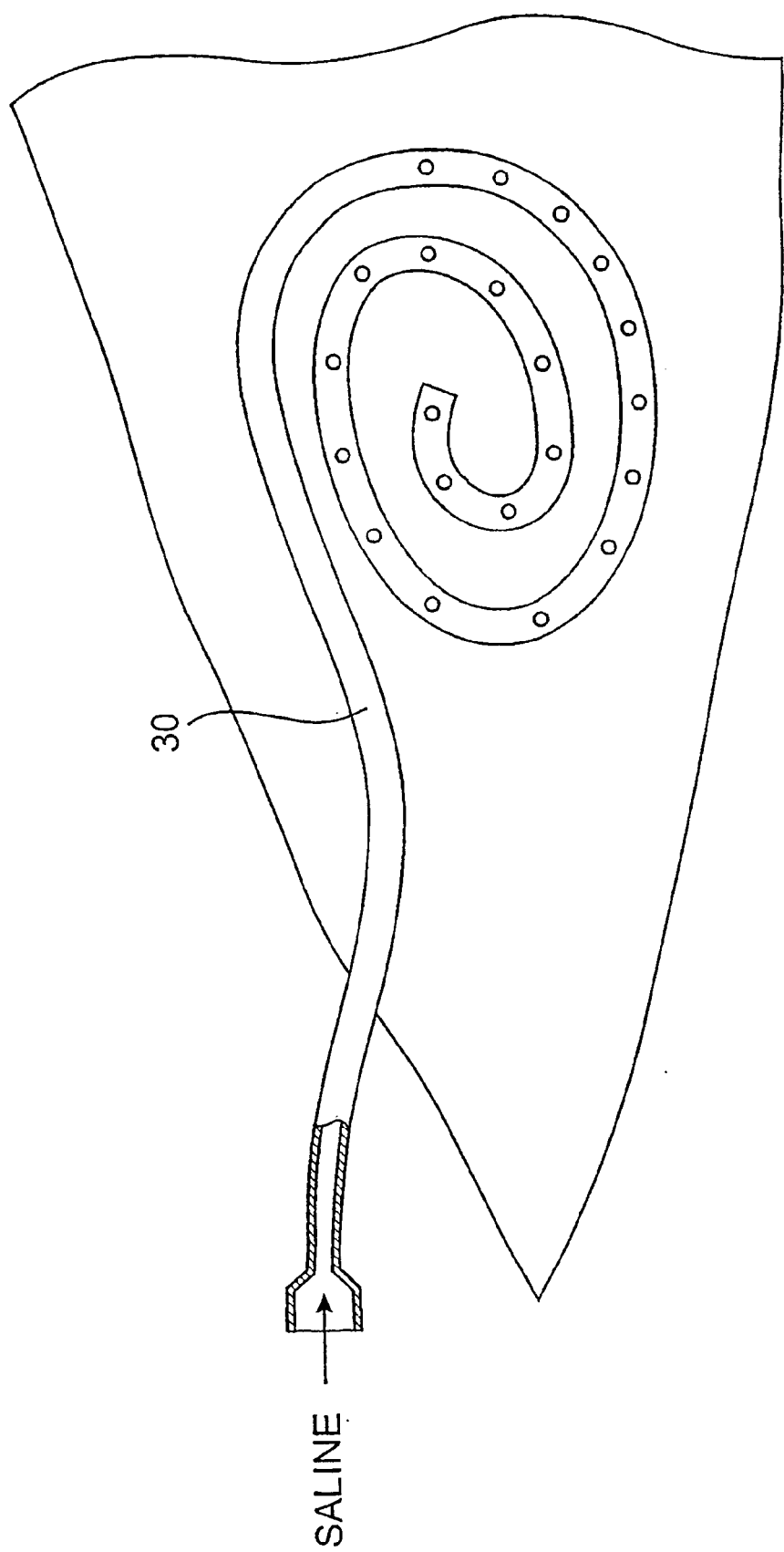
Figure 3C:
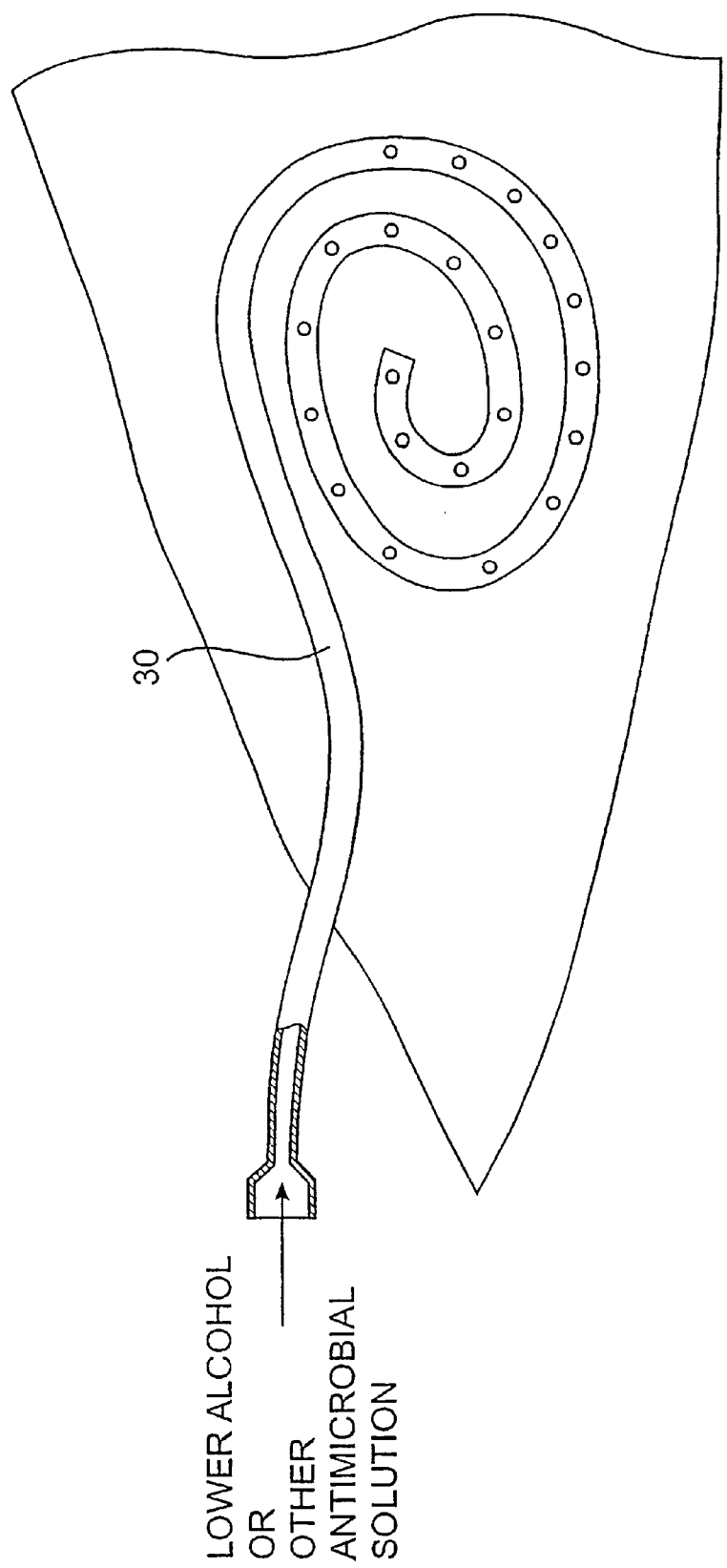

The methods of the present invention may also be used to lock non-vascular catheters, such as peritoneal dialysis catheters 30, as shown in FIGS. 3A–3C. After a peritoneal dialysis treatment, the used dialysate will be withdrawn from the catheter 30, as shown in FIG. 3A. After the dialysate has been sufficiently been removed, the dialysis catheter 30 may optionally be flushed with saline, as shown in FIG. 3B. After flushing, the lower alcohol is introduced to the peritoneal dialysis catheter 30, as shown in FIG. 3C, so that it fills the lumen of the catheter, as described previously with the vascular catheters. The use of an alcohol lock for peritoneal dialysis catheters is particularly advantageous in inhibiting infections.

Figure 4:
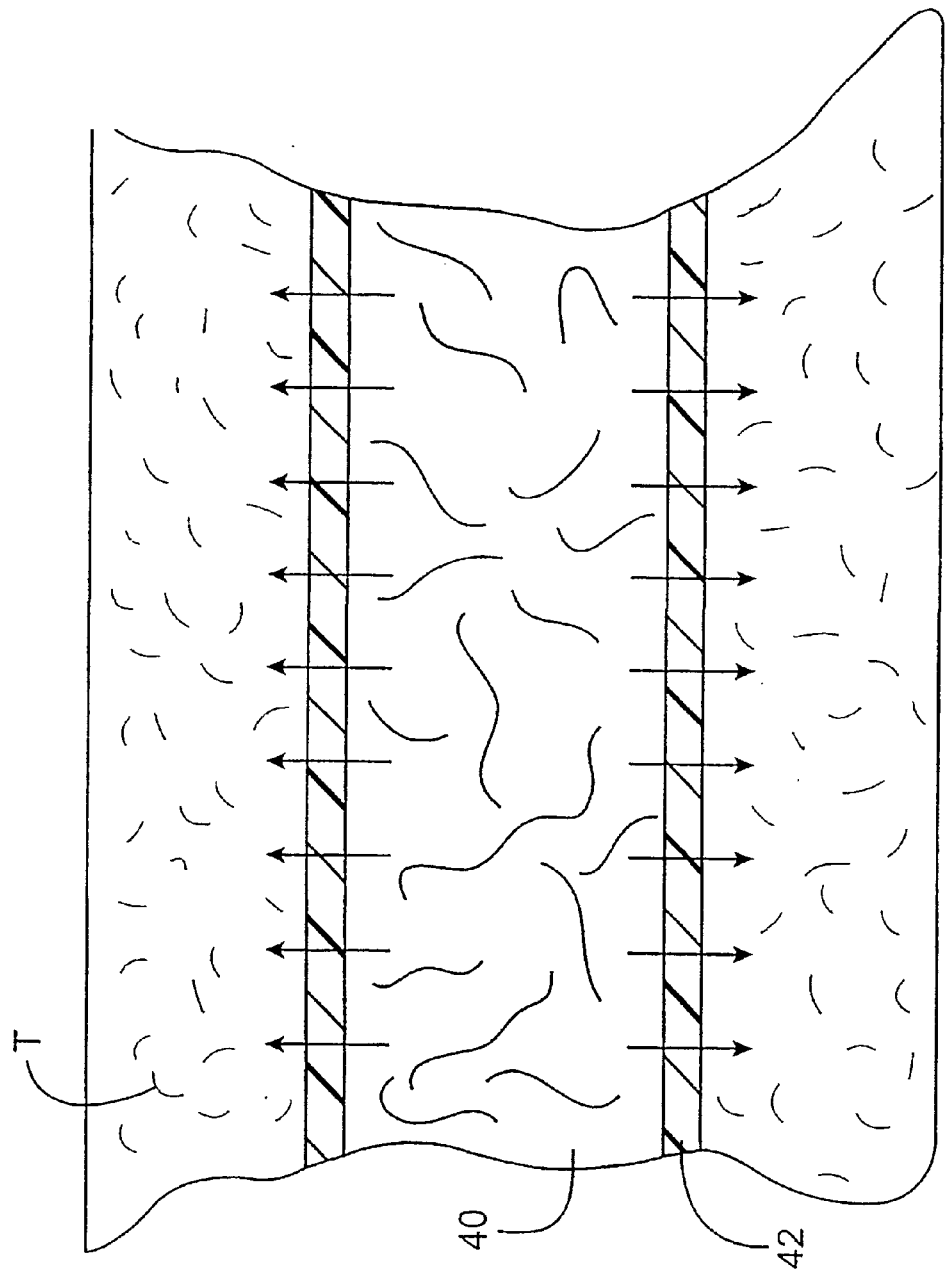
FIG. 4 illustrates a preferred aspect of the present invention where an anti-microbial locking fluid permeates into an implanted catheter body and preferably into the tissue surrounding the catheter body.

Referring now to FIG. 4, the use of lower alcohols and other anti-microbial materials for locking a catheter can be enhanced by utilizing an implanted catheter which is formed at least partly from a porous material. When the lumen 40 of the porous catheter body 42 is filled with a lower alcohol, the alcohol will be able to penetrate into the catheter body and preferably outwardly into the tissue T surrounding the catheter, as shown by the arrows in FIG. 4. Thus, the anti-microbial properties of the lower alcohols will not be limited to the interior lumen of the catheter, but will also be effective on the surface of the catheter and in the tissue region immediately surrounding the catheter body. Particularly suitable materials and porosity properties for the catheter bodies have been set forth above.

Figure 5:
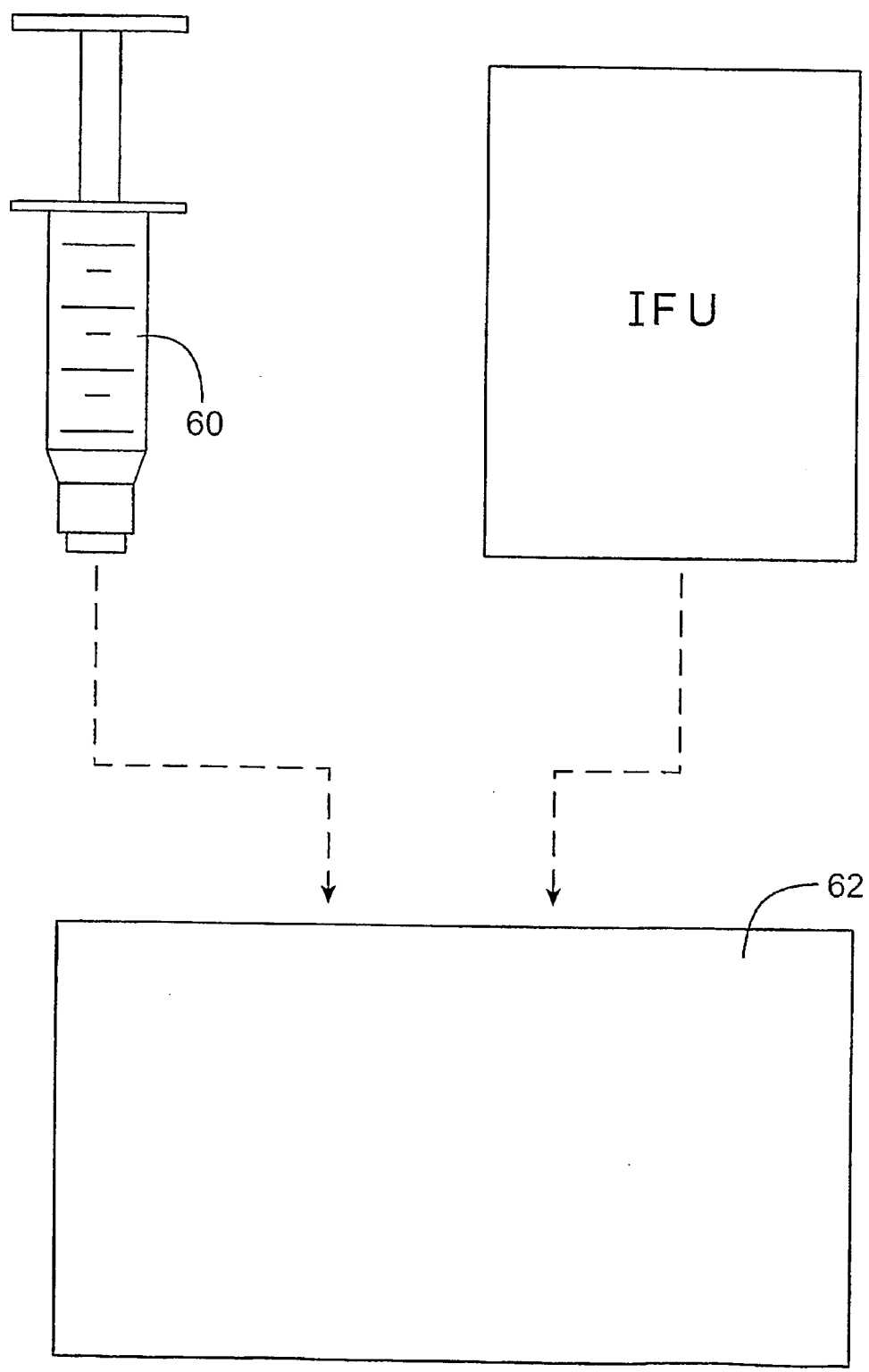
FIG. 5 illustrates a kit constructed in accordance with the principles of the present invention.

Referring now to FIG. 5, kits according to the present invention will comprise at least a container 60, such as a syringe, for holding a volume of the lower alcohol. The volume will typically be within the ranges set forth above. In addition, the kit will contain instructions for use (IFU) setting forth a method for locking and/or disinfecting an implanted catheter by introducing the lower alcohol from the container into a lumen of the catheter body between successive uses of the catheter. Usually, the kits will further contain a package 62, such as any conventional medical device package, including boxes, tubes, trays, pouches and the like.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for inhibiting infection of an implanted catheter, said method comprising filling a lumen of the catheter while open to a body lumen with an amount of a lower alcohol selected to completely fill the lumen with minimum excess alcohol passing from a distal end of the catheter into the body lumen, wherein the lower alcohol is injected to the catheter lumen.

2. A method as in claim 1, wherein the lower alcohol is selected from the group consisting of ethanol, propanol, and butanol.

3. A method as in claim 2, wherein the lower alcohol is isopropanol.

4. A method as in any of claims 1 to 3, wherein the implanted catheter is a transcutaneous catheter open to the body lumen.

5. A method as in claim 4, wherein the catheter is open to blood flow in a blood vessel.

6. A method as in claim 4, wherein the catheter is open to the peritoneal cavity.

7. A method as in any of claims 1 to 3, wherein the implanted catheter is a subcutaneous catheter implanted between a subcutaneous port and the body lumen.

8. A method as in claim 7, wherein the catheter is open to blood flow in a blood vessel.

9. A method as in claim 7, wherein the catheter is open to the peritoneal cavity.

10. A method as in claim 7, wherein the alcohol is introduced with a needle that disperses the alcohol in the port and tissue tract leading to the port as the needle is withdrawn from the port.

11. A method for inhibiting infection of an implanted catheter, said method comprising filling completely a lumen of the catheter while the catheter is open to a body lumen with isopropanol, wherein the isopropanol is inected to the catheter lumen.

12. A method as in claim 11, wherein the implanted catheter is a transcutaneous catheter open to the body lumen.

13. A method as in claim 12, wherein the catheter is open to blood flow in a blood vessel.

14. A method as in claim 12, wherein the catheter is open to the peritoneal cavity.

15. A method as in claim 11, wherein the implanted catheter is a subcutaneous catheter implanted between a subcutaneous port and the body lumen.

16. A method as in claim 15, wherein the catheter is open to blood flow in a blood vessel.

17. A method as in claim 15, wherein the catheter is open to the peritoneal cavity.

18. A method as in claim 15, wherein the isopropanol is introduced with a needle that disperses the alcohol in the port and tissue tract leading to the port as the needle is withdrawn from the port.

19. A method for inhibiting infection of an implanted catheter, said method comprising filling a lumen of a transcutaneous catheter open to a body lumen with a lower alcohol, wherein the lower alcohol is injected to the catheter lumen.

20. A method as in claim 19, wherein the lower alcohol is selected from the group consisting of ethanol, propanol, and butanol.

21. A method as in claim 20, wherein the lower alcohol is isopropanol.

22. A method as in claim 19, wherein the catheter is open to blood flow in a blood vessel.

23. A method as in claim 19, wherein the catheter is open to the peritoneal cavity.

24. A method for inhibiting infection of an implanted catheter, said method comprising filling a lumen of a subcutaneous catheter implanted between a subcutaneous port and a body lumen with a lower alcohol.

25. A method as in claim 24, wherein the lower alcohol is selected from the group consisting of ethanol, propanol, and butanol.

26. A method as in claim 25, wherein the lower alcohol is isopropanol.

27. A method as in claim 24, wherein the catheter is open to blood flow in a blood vessel.

28. A method as in claim 24, wherein the catheter is open to the peritoneal cavity.

29. A method as in claim 24, wherein the alcohol is introduced with a needle that disperses the alcohol in the port and tissue tract leading to the port as the needle is withdrawn from the port.

30. A method for inhibiting infection of an implanted transcutaneous catheter, said method comprising filling a lumen of the catheter while the catheter is open to a body lumen selected from the group consisting of a blood vessel and a peritoneal cavity with an amount of a lower alcohol selected to completely fill the lumen with minimum excess alcohol passing from a distal end of the catheter into the body lumen, wherein the lower alcohol is injected to the catheter lumen.

31. A method as in claim 30, wherein the lower alcohol is selected from the group consisting of ethanol, propanol, and butanol.

32. A method as in claim 31, wherein the lower alcohol is isopropanol.

33. A method for inhibiting infection of an implanted subcutaneous catheter, said method comprising filling a lumen of the catheter while the catheter is implanted between a subcutaneous port and a body lumen with an amount of a lower alcohol selected to completely fill the lumen with minimum excess alcohol passing from a distal end of the catheter into the body lumen.

34. A method as in claim 33, wherein the lower alcohol is selected from the group consisting of ethanol, propanol, and butanol.

35. A method as in claim 34, wherein the lower alcohol is isopropanol.

36. A method as in claim 33, wherein the catheter is open to blood flow in a blood vessel.

37. A method as in claim 33, wherein the catheter is open to the peritoneal cavity.

38. A method as in claim 33, wherein the alcohol is introduced with a needle that disperses the alcohol in the port and tissue tract leading to the port as the needle is withdrawn from the port.

* * * * *